(12) United States Patent
Ghosh et al.

(10) Patent No.: US 7,671,182 B2
(45) Date of Patent: Mar. 2, 2010

(54) GENE VARIANTS OF SIGNAL TRANSDUCER AND ACTIVATOR OF TRANSCRIPTION-6 (STAT 6) VARIANTS AND PROCESS OF DETECTION THE SAME

(75) Inventors: Balram Ghosh, New Delhi (IN); Rana Nagarkatti, New Delhi (IN); Chandrika B. Rao, New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 580 days.

(21) Appl. No.: 10/814,002

(22) Filed: Mar. 30, 2004

(65) Prior Publication Data

US 2005/0136418 A1 Jun. 23, 2005

(51) Int. Cl.
*C12Q 1/68* (2006.01)
*C07H 21/04* (2006.01)
(52) U.S. Cl. .................................. 536/23.1; 435/6
(58) Field of Classification Search .......... None
See application file for complete search history.

(56) References Cited

FOREIGN PATENT DOCUMENTS

WO WO00/62736 * 10/2000

OTHER PUBLICATIONS

AH006951—Genbank printout.*
Sequence alignments—SEQ ID No. 1 and 2.*
Nagarkatti et al. (Journal of Human Genetics, 2002, vol. 47, p. 684-687).*
Patel et al. (Genomics, 1998, vol. 52, p. 192-200).*
AH006951—Genbank printout, 2007.*
Sequence alignments—SEQ ID No. 1 and 2, 2007.*

* cited by examiner

*Primary Examiner*—Gary Benzion
*Assistant Examiner*—Stephanie K Mummert
(74) *Attorney, Agent, or Firm*—Abelman, Frayne & Schwab

(57) ABSTRACT

The present invention relates to allelic variants of the human Signal Transducer and Activator of Transcription-6 (STAT6) gene and provides primers and methods suitable for the detection of these allelic variants for applications such as molecular diagnosis, prediction of an individual's disease susceptibility, and /or the genetic analysis of the STAT6 gene in a population. Specifically, the invention provides a method for detection of predisposition to atopic disorders/other immunological disorders such as, autoimmune disorders, inflammatory disorders, fibrosis, etc. where STAT6 plays an important role by screening for human Signal Transducer and Activator of Transcription-6 (STAT 6) gene variants.

2 Claims, 4 Drawing Sheets

SEQUENCE LISTING

<160> NUMBER OF SEQ ID NOS: 7

<210> SEQ ID NO 1
<211> LENGTH: 392
<212> TYPE: DNA
<213> ORGANISM: Human
<220> FEATURE:
<221> NAME/KEY: gene
<222> LOCATION: (1)..(392)
<223> OTHER INFORMATION: Natural sequence
<220> FEATURE:
<221> NAME/KEY: Nucleotide
<222> LOCATION: (1)..(392)
<223> OTHER INFORMATION: Natural sequence

<400> SEQUENCE: 1
ttgttacagc agccctagca aactgataca ctcaccaaat cgattttgtg actcactatt    60
gggttgtaac cagcagtaca tagacataaa gttattttt ccttacgctt tatcttgtgc   120
aatcgtgtgt gtgtgtgtgt gtgtgtgtgt gtgtgtgtgt gtgtgtgtga cggagtcttg   180
ttctgtcacc aggctggagt gcagtggctt gatctcggct cactataatc acagccttcc   240
agattcaagt gatttccctg cctcagcctc ctgagtagct gggactacag gcgcgcacca   300
ccacgcccga ctaatttttt gtattttag tagagacggg gtttcaccat gttggccagg   360
atggtctcaa tctcctgacc ttgtgatctg cc                                392

<210> SEQ ID NO 2
<211> LENGTH: 336
<212> TYPE: DNA
<213> ORGANISM: Human
<220> FEATURE:
<221> NAME/KEY: Gene
<222> LOCATION: (1)..(336)
<223> OTHER INFORMATION: Natural sequence
<220> FEATURE:
<221> NAME/KEY: Nucleotide
<222> LOCATION: (1)..(336)
<223> OTHER INFORMATION: Natural sequence

<400> SEQUENCE: 2
agggagggac ctgggtagaa ggagaagccg gaaacagcgg gctggggcag ccactgctta    60
cactgaagag ggaggacggg agaggagtgt gtgtgtgtgt gtgtgtgtgt gtgtgtatgt   120
atgtgtgtgc tttatcttat ttttcttttt ggtggtggtg ttggaagggg ggaggtgcta   180
gcagggccag ccttgaactc gctggacaga gctacagacc tatggggcct ggaagtgccc   240
gctgagaaag ggagaagaca gcagaggggt tgccgaggtg aggggttgcc tccgaggtgg   300 gtgcggggc ctctatgagt gcatggggt ggattc                              336

<210> SEQ ID NO 3
<211> LENGTH: 42
<212> TYPE: DNA
<213> ORGANISM: Artificial Sequence
<220> FEATURE:
<223> OTHER INFORMATION: Forward primer for SEQ ID No. 1
<220> FEATURE:
<221> NAME/KEY: Nucleotide
<222> LOCATION: (1)..(42)
<223> OTHER INFORMATION: Forward primer for SEQ ID No. 1
<220> FEATURE:
<221> NAME/KEY: nucleotide
<222> LOCATION: (1)..(42)
<223> OTHER INFORMATION: Forward primer for SEQ ID No. 1

<400> SEQUENCE: 3

-continued

```
tgtaaaacga cggccagttt gttacagcag ccctagcaaa ct                42
```

<210> SEQ ID NO 4
<211> LENGTH: 24
<212> TYPE: DNA
<213> ORGANISM: Artificial Sequence
<220> FEATURE:
<223> OTHER INFORMATION: Reverse primer for SEQ ID No. 1
<220> FEATURE:
<221> NAME/KEY: Nucleotide
<222> LOCATION: (1)..(24)
<223> OTHER INFORMATION: Reverse primer for SEQ ID No. 1

<400> SEQUENCE: 4

```
ggcagatcac aaggtcagga gatt                                   24
```

<210> SEQ ID NO 5
<211> LENGTH: 41
<212> TYPE: DNA
<213> ORGANISM: Artificial Sequence
<220> FEATURE:
<223> OTHER INFORMATION: Forward Primer for SEQ ID No. 2
<220> FEATURE:
<221> NAME/KEY: Nucleotide
<222> LOCATION: (1)..(41)
<223> OTHER INFORMATION: Forward Primer for SEQ ID No. 2

<400> SEQUENCE: 5

```
tgtaaaacga cggccagtag ggagggacct gggtagaagg a                 41
```

<210> SEQ ID NO 6
<211> LENGTH: 24
<212> TYPE: DNA
<213> ORGANISM: Artificial Sequence
<220> FEATURE:
<223> OTHER INFORMATION: Reverse primer for SEQ ID no. 2
<220> FEATURE:
<221> NAME/KEY: Nucleotide
<222> LOCATION: (1)..(24)
<223> OTHER INFORMATION: Reverse primer for SEQ ID no. 2
<220> FEATURE:
<221> NAME/KEY: Nucleotide
<222> LOCATION: (1)..(24)
<223> OTHER INFORMATION: Reverse primer for SEQ ID no. 2

<400> SEQUENCE: 6

```
gaatccaccc ccatgcactc atag                                   24
```

<210> SEQ ID NO 7
<211> LENGTH: 18
<212> TYPE: DNA
<213> ORGANISM: Artificial Sequence
<220> FEATURE:
<223> OTHER INFORMATION: Fluorescent labelled M13 primer
<220> FEATURE:
<221> NAME/KEY: Nucleotide
<222> LOCATION: (1)..(18)
<223> OTHER INFORMATION: Fluorescent labelled M13 primer

<400> SEQUENCE: 7

```
tgtaaaacga cggccagt                                          18
```

GENE VARIANTS OF SIGNAL TRANSDUCER AND ACTIVATOR OF TRANSCRIPTION-6 (STAT 6) VARIANTS AND PROCESS OF DETECTION THE SAME

FIELD OF INVENTION

The present invention is concerned with the detection and utilization of the allelic variants of the human STAT6 gene with the aim of predicting an individual's susceptibility to develop asthma. More specifically, the present invention relates to allelic variants of the human Signal Transducer and Activator of Transcription-6 (STAT6) gene and provides primers and methods suitable for the detection of these allelic variants for the prediction of an individual's disease susceptibility, and /or the genetic analysis of the STAT6 gene in a population. Thus the method provides for detection of predisposition to atopic disorders by screening for human Signal Transducer and Activator of Transcription-6 (STAT 6) gene variants.

BACKGROUND INFORMATION

The genomic DNA of all organisms undergoes spontaneous changes in the sequence (termed as mutation) in the course of their continuing evolution thereby generating variant forms of progenitor sequences, which may lead to various evolutionary advantages or disadvantages to the survival of the organism. If such effects of the mutations or variations are not seen then they are termed as neutral changes/mutations. If the mutation is lethal then it is not transmitted to the following generations and thus the mutation is lost from the gene pool of that organism. A variant form may also confers an evolutionary advantage to the species and is eventually incorporated into the DNA of many or most members of the species, and hence, effectively it becomes the progenitor form. In many instances, both progenitor and variant form(s) survive and co-exist in the gene pool of the species. This coexistence. of multiple forms of a sequence gives rise to polymorphisms.

Several different types of polymorphism have been reported. A restriction fragment length polymorphism (RFLP) means a variation in DNA sequence that alters the length of a restriction fragment. The restriction fragment length polymorphism may create or delete a restriction site, thus changing the length of the restriction fragment. RFLPs have been widely used in human and animal genetic analyses. Other polymorphisms take the form of short tandem repeats (STRs) that include tandem di-, tri- and tetranucleotide repeated motifs. These tandem repeats are also referred to as variable number tandem repeat (VNTR) polymorphisms. VNTRs have been used in identity and paternity analysis and in a large number of genetic mapping studies. Other polymorphisms take the form of single nucleotide variations. Such polymorphisms are far more frequent than RFLPS, STRs and VNTRs. Some single nucleotide polymorphisms (SNPs) occur in protein-coding sequences, in which case, one of the polymorphic forms may give rise to the expression of a defective or other variant protein and, potentially, a genetic disease. Examples of genes, in which polymorphisms within coding sequences give rise to genetic disease include beta-globin (sickle cell anemia) and CFTR (cystic fibrosis). Other single nucleotide polymorphisms occur in noncoding regions. Some of these polymorphisms may also result in defective protein expression (e.g., as a result of defective splicing). Other single nucleotide polymorphisms have no phenotypic effects.

The effects of such polymorphisms can be at various levels of cellular organization. Polymorphic elements in the promoter and/or regulatory regions are known to modulate the levels of mRNA of the genes. Polymorphisms in the untranslated regions (UTR's) of the RNA have also been documented to regulate the transcriptional and translational rates of the genes. Their presence in the intron-exon boundaries can also lead to changes in splicing and or splice products that are formed from the native full length mRNA. Polymorphisms in the coding region may change the function of the protein if it is a non-synonymous change and if it occurs in a critical domain of the protein leading to functional changes of the protein.

Thus polymorphisms are useful in defining genomic regions (for example as genetic markers) and they may also lead to disease (for example functional polymorphisms). Numerous examples are documented in the scientific literature and persons trained in this field are familiar with it (please see Abney M et al, Am J Hum Genet 70:920-34, 2002; Baron M, Mol Psychiatry 6:143-9, 2001; Bodmer W F, Ciba Found Symp 130:215-28, 1987; Breslow J L, Physiol Rev 68:85-132, 1988; Caraballo L R and Hernandez M, Tissue Antigens 35:182-6, 1990; Levitt R C, Am J Respir Crit Care Med 150:S94-9, 1994; Xu J et al, Clin Exp Allergy 28 Suppl 5:1-5; discussion 26-8, 1998).

Atopic diseases are a clinically heterogeneous group of diseases characterized by elevated serum IgE levels and varying phenotypic expressions such as Asthma and Atopic Dermatitis (Barnes K C, Clin Exp Allergy 29 Suppl 4:47-51 1999; Barnes P J Respir Res 2:64-5, 2001; Blumenthal M N and Amos D B, Chest 91:176S-184S, 1987; Thomas N S et al, Am J Respir Crit Care Med 156:S144-51, 1997). Specifically, Asthma is a chronic airway disease, affecting 15-18% of the world's population.

It is mainly a childhood disorder though the age. of onset can vary and is seen to be 35-45 yr. in the general population. Another case of extrinsic asthma is observed where the age of onset is above 45 yr. and is mainly due to the age induced changes in the lung function. The pathophysiology of atopic asthma is well documented. It is a T helper type 2 (Th2) mediated disorder with cytokines such as interleukin-4, interleukin-5, interleukin-13, implicated in the deviation of the immune system towards atopicity. Increased levels of these cytokines lead to elevated total serum IgE levels, eosinophil recruitment, and bronchial hyper-responsiveness that ultimately culminate in asthma pathogenesis. These interleukins are also known to interact and stimulate the alveolar cells and bronchial smooth muscle cells resulting in the clinical phenotypes of bronchial hyper-responsiveness (Barnes P J, Respir Res 2:64-5, 1999). Gene-gene and gene-environment interactions have been implicated in the development of asthma (Tay et al, Asian Pac J Allergy Immunol 17:239-42, 1999; Bleecker E R, Am J Respir Crit Care Med 156:S113-6, 1997; Cookson W, Nature 402:B5-11, 1999).

Various genetic studies have shown multiple loci to be associated with the disease. Asthma is therefore a multigenic disorder with a number of genes contributing minor effects leading to pathogenesis. Linkage studies, in various populations, have narrowed down the presence of susceptibility or disease genes to chromosomal locations such as 1p31, 5q31-33, 1p13, 12q13-24, 13q14, 17q12-21. However, all the causative genes and mutations have so far not been identified (Bleecker E R et al, Am J Respir Crit Care Med 156:S113-6, 1997; Blumenthal M N, Chest 91:176S-184S, 1987, Duffy D L, Epidemiol Rev 19:129-43, 1997).

Moreover, there is evidence to suggest that ethnic differences exist in the susceptibility genes associated with asthma (Xu J et al, Am J Hum Genet 68:1437-46, 2001). Of these loci, 12q21-23 harbors the Signal Transducer and Activator of Transcription-6 (STAT6) gene (consisting of 23 exons spanning a region of 19 kbp) which is thought to be an important candidate gene. STAT6 plays a major role in the initiation of signals from activated Th2 cells, specifically through IL4 and IL13 receptors (Ihle J N, Curr Opin Cell Biol 13:211-7, 2001; Zhu J et al, J Immunol 166:7276-81, 2001; Horvath C M, Trends Biochem Sci 25:496-502, 2000). STAT6 has also been implicated in the differential expression of chemokines, such as eotaxin-1, eotaxin-2 and thymus and activation regulated chemokine (TARC) (Takeda K and Akira S, Cytokine Growth Factor Rev 11:199-207, 2000; Zhang S et al, J Immunol 165:10-4, 2000; Mathew A et al, J Exp Med 193:1087-96, 2001). It is expressed in activated T cells in response to anti-CD3 antibody, PMA and other mitogenic responses (Arinobu Y et al, Biochem Biophys Res Commun 277:317-24, 2000). Interleukin 4 Receptor alpha (IL4RA) mediated phosphorylation of the STAT6 leads to its dimerization and nuclear localization, where it binds to the promoter elements of the Cϵimmunoglobulin gene and causes the expression of the ϵ-transcript (Paul W E, Ciba Found Symp 204:208-16, discussion 216-9, 1997; Nelms K et al, Annu Rev Immunol 17:701-38, 1999; Linehan L A et al, J Immunol 161:302-10, 1998; Yang M et al, Am J Respir Cell Mol Biol 25:522-30, 2001).

Two naturally occurring isoforms have been detected that may modulate IL4 induced functional responses and cellular proliferation (Sherman M A et al, J Immunol 162:2703-8, 1999; Mullings R E et al, J Allergy Clin Immunol 108:832-8, 2001). The significance of this pathway in the development of atopic responses has been demonstrated by the failure of STAT6 (−/−) mice to develop a Th2 response, including, a lack in IgE production and eosinophilia, and failure to develop airway hyper-responsiveness in response to antigen challenge (Akimoto T et al, J Exp Med 187:1537-42, 1998; Miyata S et al, Clin Exp Allergy 29:114-23, 1999; Tomkinson A et al, Am J Respir Crit Care Med 160:1283-91, 2002; Zhu J et al, J Immunol 166:7276-81, 2001). A STAT6 antisense oligonucleotide was also shown to down regulate the expression of the germline ϵ transcript in DND39, a human Burkitt lymphoma cell line (Hill S et al, Am J Respir Cell Mol Biol 21:728-37, 1999).

Case control studies in the Japanese population have shown that a dinucleotide repeat in the 5' UTR of this gene to be associated with asthma and atopic disorders (Gao P S et al, J Med Genet 37:380-2, 2000; Tamura K et al, Clin Exp Allergy 31:1509-14, 2001). However, they have not found any association of the repeat size with the total serum IgE levels. Also, this observation has not been confirmed in a more stringent study on a Caucasian sib pair cohort (Duetsch G et al, Hum Mol Genet 11:613-21, 2002). Duetsch et al has sequenced the complete gene and have identified a set of 23 SNPs spanning the intronic region. They have however not identified a polymorphism in the coding region. They were not able to demonstrate a significant association of these polymorphisms with asthma. These two studies suggest that there is a component of ethnic variation that is involved and that depends on the particular population under study.

In an earlier case control study in the Japanese population, the R3 locus has been found to be associated with asthma (13 repeat allele) (Tamura K et al, Clin Exp Allergy 31:1509-14, 2001). However, in a sib pair study in a German population, no such association of the R3 locus with asthma was seen, although weak associations were observed for the total serum IgE levels and the eosinophil counts with the alleles 17 and 16, respectively (Duetsch G et al , Hum Mol Genet 11:613-21, 2002). The present results of the present study provide very unique and unexpected results as shown in the prior arts. The association of allele 15 with asthma in the population could be explained are based not only on the ethnic differences that exist between observed in the present population and the Japanese and the Caucasian populations, but found generally in any population of the world. The present has identified the variants, which exist in any type of population in the world irrespective of its origin, community, colour, geographical location or ethnicity. The inventors have compared allele frequencies at R1 and R3 loci, and their haplotypes, in a population (comprising population from both North and South parts of India), they observed that their distributions are significantly different (data not shown). Also, the sampling strategies used in the studies are different. The present study is a case control study although the inventors have recruited individuals with a familial history of asthma and atopy. Further, the invention clearly defines that the variants identified would be useful for any kind of population of any geographical origin.

It is apparent that the use of the R1 and R3 polymorphisms in the generation of haplotypes in conjunction with SNP data for this gene may yield more informative haplotypes. The haplotypes of SNPs obtained in the German population suggests that there may be a recombination hot spot in the gene (Duetsch G et al, Hum Mol Genet 11:613-21, 2002). Estimation of decay of LD across the putative recombination hot spot could have been important in defining functional aspects of this genomic region. In any event, if functional polymorphisms are present on the chromosomal background of specific haplotypes then haplotypes that describe parts of the STAT6 gene flanking the putative recombination hot spot may provide a better association with asthma and total IgE. However, this hypothesis remains to be tested in the future.

Both the R1 and R3 polymorphisms seem to be biologically relevant. Using promoter deletion analysis it has been shown that the RI locus is flanked by the critical transcription factor binding sites TFIIIA and the TATA box (Patel B K et al, Genomics 52:192-200, 1998). Moreover, di-nucleotide repeats are known to bind various minor groove-binding proteins, which can interact with the basal transcriptional complex may modulate transcription. Interestingly, it has been shown that dinucleotide repeats have a propensity for forming Z-DNA like structures and that in the promoter regions these are capable of regulating transcription, for example, in the rat nucleolin gene (Rothenburg S et al, Proc Natl Acad Sci USA 98:8985-90, 2001). Also, CA repeats in the intron are known to regulate gene expression, for example in the first intron of epidermal growth factor receptor gene and interferon gamma genes (Gebhardt F et al, J Biol Chem 274:13176-80, 1999).

Similarly, the 5'-UTR is known to regulate translation of various genes through interaction with protein factors or by pseudoknot formation (Mokdad-Gargouri R et al, Nucleic Acids Res 29:1222-7, 2001; Ben-Asouli Y et al, Cell 108: 221-32, 2002). However, further experimental work needs to be done to provide a conclusive proof for these hypotheses. In this context, it is important to note that, as shown by other groups and in the present study, no coding variants of STAT6 gene were found (Heinzmann A Clin Exp Allergy 30:1555-61, 2000, Duetsch G et al, Hum Mol Genet 11:613-21, 2002, Nagarkatti R and Ghosh B, 2002, in press). Thus it is possible that the action of STAT6 may be mediated mostly by the transcriptional and translation modulation of its levels, rather than due to structural changes in the protein itself. Thus, based on the above evidence it appears that STAT6 may be an important modifier locus that plays a significant role in regulating the atopic phenotypes depending on the ethnic background of the patients.

OBJECTS OF THE INVENTION

The main object of the present invention provides novel gene variants of Signal Transducer and Activator of Transcription-6 (STAT 6) gene responsible for atopic disorders.

Another object of the invention is to provide a method for detecting the predisposition to atopic disorders by STAT-6 gene variants in a population.

Yet another object of the present invention provides a method detecting gene variants of STAT-6 gene for predicting susceptibility of a subject to atopic disorders.

Still another object of the present invention provides specific primers and probes for detection of single nucleotide polymorphisms in the STAT6 gene.

One more object of the present invention provides the haplotypes generated by the allelic variants of the STAT6 gene in the general population.

Yet another object of the invention provides a method for studying association of the haplotypes of the STAT6 allelic variants with disease susceptibility.

Another object of the present invention provides pharmacogenetic markers for detecting and predicting predisposition to atopic disorders One more object of the present invention relates to a diagnostic kit detecting and predicting predisposition to atopic disorders.

SUMMARY OF THE INVENTION

Atopic diseases are a clinically heterogeneous group of diseases characterized by elevated serum IgE levels and varying phenotypic expressions such as asthma, allergy and atopic dermatitis. Various genetic and environmental factors are known to affect the disease process. Thus for such complex disorders it is thought that there are numerous factors that contribute to cause the disease. These interactions may be synergistic, antagonistic, epistatic etc. Of the genetic factors human signal transducer and activator of transcription 6 gene (STAT6) is an important candidate gene for causation of susceptibility and/or pathogenesis. It is the primary molecule through which the signaling pathway of atopy-related genes and proteins is executed. The present invention relates to allelic variants of the human Signal Transducer and Activator of Transcription-6 (STAT6) gene and provides primers and methods suitable for the detection of these allelic variants for applications such as molecular diagnosis, prediction of an individual's disease susceptibility, and /or the genetic analysis of the STAT6 gene in a population. Specifically, the invention provides a method for detection of predisposition to atopic disorders/other immunological disorders such as, autoimmune disorders, inflammatory disorders, fibrosis, etc. where human Signal Transducer and Activator of Transcription-6 (STAT 6) plays an important role.

BRIEF DESCRIPTION OF THE ACCOMPANYING DRAWINGS/FIGURES

FIG. 1 shows a schematic presentation of the two di-nucleotide repeat polymorphisms in STAT6 gene. The repeat in the promoter is denoted as R1 and in the repeat polymorphism in the 5-UTR is denoted as R3. Both the polymorphisms are also shown in sequence context below the gene. The R1 and R3 loci are schematically depicted in context to the gene and the major regulatory elements in the promoter; R1 and R3 denote the repeat loci; E1, E2 and E3 denote the exons; 5'-UTR, 5' un-translated region; ATG, the first initiation codon in the protein coding region; kb, kilo-base; TFIIA, Transcription factor IIA; TFIIIA, Transcription factor IIIA; TATA box, recognition site for Eukaryotic type II RNA Polymerase; C/EBP-6 CAAT enhancer binding protein delta; CCAAT Enhancer, Trans acting DNA element required for the recruitment of transcription factors and in the assembly of the transcription complex.

Figure 4:
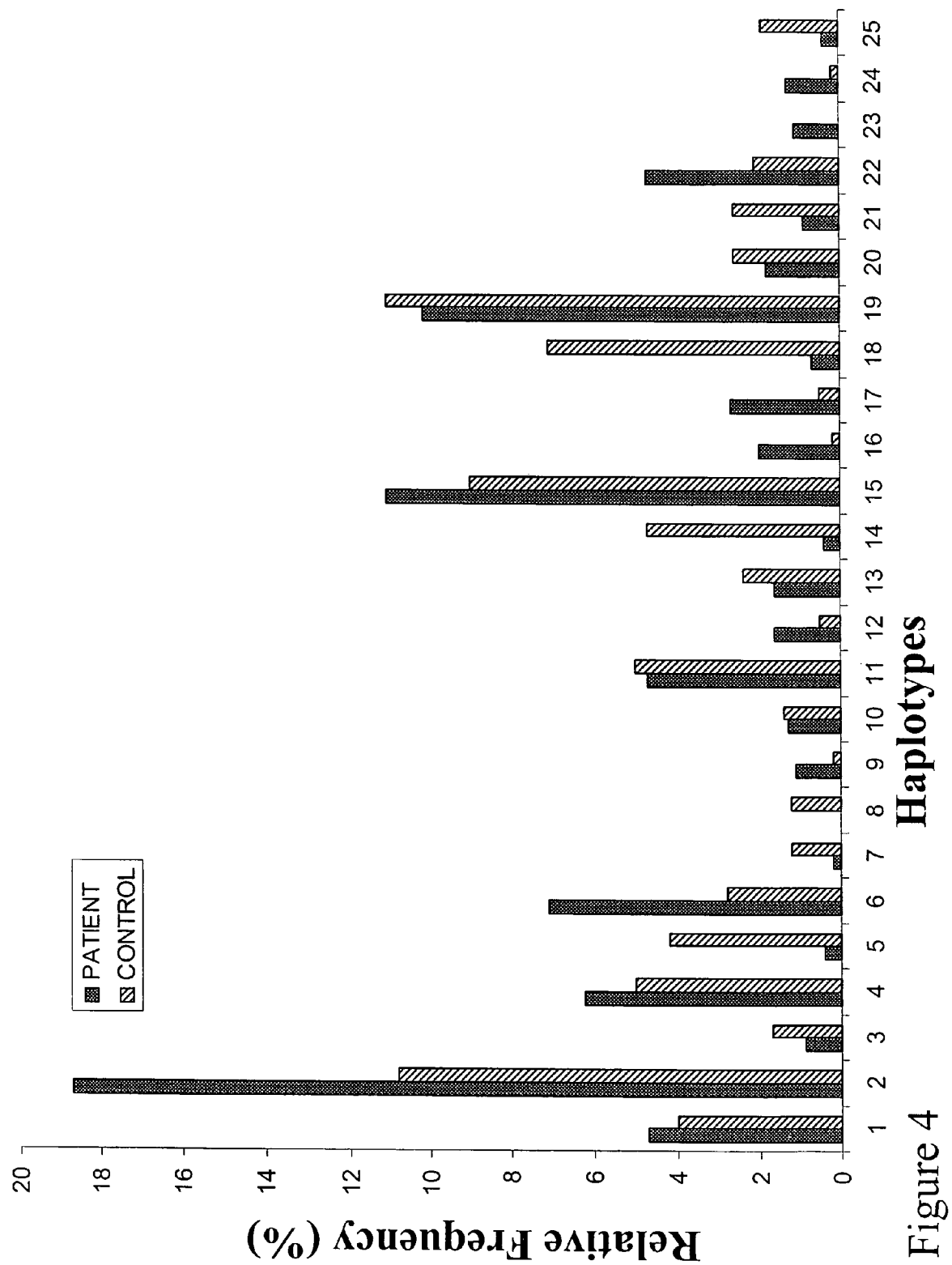

FIG. 4 shows the distribution of R1_R3 haplotypes in 349 normal chromosomes and 386 asthmatic patient chromosomes (Table 3). The figure depicts the haplotype frequencies generated using the PHASE software on the data set of control and patient R1 and R3 loci (denoted as R1_R3, i.e. in genomic order). The haplotypes have been denoted with numerical codes 1 to 29 on the X-axis and their respective frequencies on the Y-axis. The codes stand for the haplotypes listed in Table 3.

DETAILED DESCRIPTION OF THE INVENTION

The present invention provides method of detecting allelic variants of human STAT6 gene and their association with the atopic asthma and the said method comprises the following. Specifically the method provides for the detection of predisposition to atopic disorders by screening for human Signal Transducer and Activator of Transcription-6 (STAT 6) gene variants. In an earlier case control study in the Japanese population, the R3 locus has been found to be associated with asthma (13 repeat allele) (Tamura K et al, Clin Exp Allergy 31:1509-14, 2001). However, in a sib pair study in a German population, no such association of the R3 locus with asthma was seen, although weak associations were observed for the total serum IgE levels and the eosinophil counts with the alleles 17 and 16, respectively (Duetsch G et al , Hum Mol Genet 11:613-21, 2002). The present results of the present study provide very unique and unexpected results as shown in the prior arts. The association of allele 15 with asthma in the population could be explained are based not only on the ethnic differences that exist between observed in the present population and the Japanese and the Caucasian populations, but found generally in any population of the world. The present has identified the variants, which exist in any type of population in the world irrespective of its origin, community, colour, geographical location or ethnicity. The inventors have compared allele frequencies at R1 and R3 loci, and their haplotypes, in a population (comprising population from both North and South parts of India), they observed that their distributions are significantly different (data not shown). Also, the sampling strategies used in the studies are different. The present study is a case control study although the inventors have recruited individuals with a familial history of asthma and atopy. Further, the invention clearly defines that the variants identified would be useful for any kind. of population of any geographical origin. The Table 1 provides a comparison between the present invention and the prior arts.

Accordingly, the main embodiment of the present invention provides novel gene variants having of SEQ ID Nos. 1 and 2 associated with R1 and R3 locus of Signal Transducer and Activator of Transcription-6 (STAT-6) Gene useful in predicting susceptibility of a subject to atopic disorders, said gene variants having following characteristics:
  (a) the SEQ ID No. has 1-392 contiguous nucleotides containing one or more group of GT dinucleotide polymorphisms at positions from 125 to 168 bases associated locus R1, and
  (b) the SEQ ID No. has 1 to 336 contiguous nucleotides containing one or more group of GT dinucleotide polymorphisms at positions from 87 to 116 bases associated with region containing R3 polymorphism of locus R3.

Another embodiment of the present invention relates to a method of detecting gene variants having SEQ ID Nos. 1 and 2 associated with R1 and R3 locus of STAT-6 for predicting susceptibility of a subject to atopic disorders said method comprising the steps of:
  (a) isolating DNA or RNA from samples selected from group comprising of whole blood, semen, saliva, tears, urine, fecal material, sweat, buccal, skin or hair,
  (b) designing and synthesizing primers having SEQ ID Nos. 3, 4, 5, 6 and 7
  (c) amplifying the genomic DNA or RNA using primers having SEQ ID Nos. 3, 4, 5, 6 and 7,
  (d) isolating and identifying SEQ ID No.1 using primer combinations having SEQ ID Nos. 3, 4, and 7 and SEQ ID No. 2 using primer combinations having SEQ ID Nos. 5, 6 and 7,
  (e) sequencing the isolated and identified SEQ ID Nos. 1 and 2 of step (d), and
  (f) validating and identifying the specific gene variants having SEQ ID Nos. 1 and 2 computationally by comparing with known START-6 gene, wherein the SEQ ID Nos. 1 and 2 has following characteristics
    (a) the SEQ ID No. has 1-392 contiguous nucleotides containing one or more group of GT dinucleotide polymorphisms at positions from 125 to 168 of locus R1, and
    (b) The SEQ ID No. has 1 to 336 contiguous nucleotides containing one or more group of GT dinucleotide polymorphisms at positions from 87 to 116 bases of locus R3.

Yet another embodiment of the present invention relates to a method of detecting and predicting predisposition to atopic disorders by screening locus R1 and R3 of STAT-6 gene variants in a subject, said method comprising the steps of:
  (a) isolating DNA or RNA from samples selected from group comprising of whole blood, semen, saliva, tears, urine, fecal material, sweat, buccal, skin or hair,
  (b) designing and synthesizing primers having SEQ ID Nos. 3, 4, 5, 6 and 7
  (c) amplifying the genomic DNA or RNA using primers having SEQ ID Nos. 3, 4, 5, 6 and 7,
  (d) isolating and identifying SEQ ID No.1 using primer combinations having SEQ ID Nos. 3, 4, and 7 and SEQ ID No. 2 using primer combinations having SEQ ID Nos. 5, 6 and 7,
  (e) sequencing the isolated and identified SEQ ID Nos. 1 and 2 of step (d), and
  (f) validating and identifying the specific gene variants having SEQ ID Nos. 1 and 2 computationally by comparing with known START-6 gene, wherein the SEQ ID Nos. 1 and 2 has following characteristics:
    (a) the SEQ ID No. has 1-392 contiguous nucleotides containing one or more group of GT dinucleotide polymorphisms at positions from 125 to 168 bases locus R1, and
    (b) The SEQ ID No. has 1 to 336 contiguous nucleotides containing one or more group of GT dinucleotide polymorphisms at positions from 87 to 116 bases of locus R3.

One more embodiment of the present invention relates to a method of preparing novel pharmacogenetic markers for detecting and predicting predisposition to atopic disorders by screening R1 and R3 locus of STAT-6 gene in a subject, said method comprising steps of:
  (a) isolating DNA or RNA from samples selected from group comprising of whole blood, semen, saliva, tears, urine, fecal material, sweat, buccal, skin or hair,
  (b) designing and synthesizing primers having SEQ ID Nos. 3, 4, 5, 6 and 7
  (c) amplifying the genomic DNA or RNA using primers having SEQ ID Nos. 3, 4, 5, 6 and 7,
  (d) isolating and identifying SEQ ID No.1 using primer combinations having SEQ ID Nos. 3, 4, and 7 and SEQ ID No. 2 using primer combinations having SEQ ID Nos. 5, 6 and 7,
  (e) sequencing the isolated and identified SEQ ID Nos. 1 and 2 of step, (d), and
  (f) validating and identifying the specific gene variants having SEQ ID Nos. 1 and 2 computationally by comparing with known START-6 gene, wherein the SEQ ID Nos. 1 and 2 has following characteristics:
    (a) the SEQ ID No. has 1-392 contiguous nucleotides containing one or more group of GT dinucleotide polymorphisms at positions from 125 to 168 bases of locus R1, and
    (b) The SEQ ID No. has 1 to 336 contiguous nucleotides containing one or more group of GT dinucleotide polymorphisms at positions from 87 to 116 bases of locus R3.

Still another embodiment of the present invention relates to the Pharmacogenetic markers having SEQ ID Nos. 1 and 2 for detecting and predicting predisposition to atopic disorders of STAT-6 gene in a subject said markers comprising of following characteristics:
  (a) the SEQ ID No.1 has 1-392 contiguous nucleotides containing one or more group of GT dinucleotide polymorphisms at positions from 125 to 168 of R1 locus, and
  (b) the SEQ ID No.2 has 1 to 336 contiguous nucleotides containing one or more group of GT dinucleotide polymorphisms at positions from 87 to 116 bases of R3 locus.

Another embodiment of the present invention relates to the diagnostic kit for detecting and predicting predisposition to atopic disorders by screening R1 and R3 locus of STAT-6 gene in a subject, said method comprising the steps of:
  (g) isolating DNA or RNA from samples selected from group comprising of whole blood, semen, saliva, tears, urine, fecal material, sweat, buccal, skin or hair,
  (h) designing and synthesizing primers having SEQ ID Nos. 3, 4, 5, 6 and 7
  (i) amplifying the genomic DNA or RNA using primers having SEQ ID Nos. 3,4, 5, 6 and 7,
  (j) isolating and identifying SEQ ID No.1 using primer combinations having SEQ ID Nos. 3, 4, and 7 and SEQ ID No. 2 using primer combinations having SEQ ID Nos. 5, 6 and 7,
  (k) sequencing the isolated and identified SEQ ID Nos. 1 and 2 of step (d), and (l) validating and identifying the specific gene variants having SEQ ID Nos. 1 and 2 computationally by comparing with known START-6 gene, wherein the SEQ ID Nos. 1 and 2 has following characteristics:

(a) the SEQ ID No. has 1-392 contiguous nucleotides containing one or more group of GT dinucleotide polymorphisms at positions from 125 to 168 bases of locus R1, and (b) The SEQ ID No. has 1 to 336 contiguous nucleotides containing one or more group of GT dinucleotide polymorphisms at positions from 87 to 116 bases of locus R3.

Yet another embodiment of the present invention relates to the gene variants of SEQ ID Nos. 1 and 2, wherein the SEQ ID No. 1 is associated with R1 locus and SEQ ID No. 2 is associated with R3 locus of STAT-6 gene Another embodiment of the present invention relates to a subject wherein a subject is a human.

Yet another embodiment of the present invention relates to the atopic disorders wherein atopic disorders are selected are from group comprising of asthma, atopic dermatitis, autoimmune disorders, inflammatory disorders, fibrosis or other known disorder of STAT-6 gene.

One more embodiment of the present invention relates to the atopic disorder wherein atopic disorder is asthma.

Still another embodiment of the present invention relates to the novel gene variants wherein said variants are useful are predicting and detecting humans susceptible to asthma.

Another embodiment of the present invention relates to the R1_R3 locus wherein the percentage frequency of R1_R3 locus dinucleotide on allele 17__15 and 16__15 is about 8% and 20%, respectively in the patients.

Still another embodiment of the present invention relates to the R1_R3 locus, wherein the percentage frequency of R1_R3 locus dinucleotide on allele 17__15 and 16__15 is about 7.1% and 18.7%, respectively in the patients.

One more embodiment of the present invention relates to the novel gene variants wherein said gene variants associated with specific haplotypes 17__15 and 16__15 where CA repeat is on allele 17 is of R1 locus and 15 of R3 locus of the Stat 6 gene with 'p' value less than 0.0031 and are associated with asthma.

Still another embodiment of the present invention relates to the gene variants wherein gene variant haplotypes 17__14 (CA repeat 17 in R1 locus and 14 in R3 locus of the STAT-6 gene having a 'p' value less than 0.00001), 23__16 (CA repeat 23 in R1 locus and 16 in R3 locus of the STAT-6 gene having a 'p' value less than 0.00001) and 24__16 (CA repeat 24 in R1 locus and 16 in R3 locus of the STAT-6 gene having a 'p' value less than 0.00001) are associated with protection from asthma.

Another embodiment of the present invention relates to the novel gene variants as wherein said gene variants of locus R1_R3 are associated with specific haplotypes 17__15 and 16__15

TABLE 1

Comparative Table differentiating present invention from prior inventions

| Known Repeats | Known associations Reported in Prior Arts | Present Invention on R3 Repeat | Present invention (Repeats) | Known Haplotypes | Haplotypes of the present invention | As claimed in present |
|---|---|---|---|---|---|---|
| R3 | 1) 13 allele locus of R3 repeat found associated with asthma in Japanese population (Gao et al; Clin. Exp. Allergy 31: 1509-14; 2001) 2) Allele no 17 & 16 of R3 locus found associated with IgE (Duetsch et al, Hum. Mol. Genet 11: 613-21; 2002) | Allele no 15 of R3 locus found associated with asthma in a population | Novel R1 repeats identified in a population | Nil | (R1__R3) Total-29: 1, (27__17); 2, (25__15); 3, (23__18); 4, (19__17); 5, (26__16); 6, (21__17); 7, (19__19); 8, (23__14); 9, (24__14); 10, (17__17); 11, (26__17); 12, (24__15); 13, (25__14); 14, (17__16); 15, (24__18); 16, (25__17); 17, (17__15); 18, (16__17); 19, (22__16); 20, (16__16); 21, (22__17); 22, (23__17); 23, (25__16); 24, (23__16); 25, (16__14); 26, (16__15); 27, (17__14); 28, (24__16); 29(24__17). | Haplotype 17, (17__15) of R1_R3 loci found to be positively associated with asthma in Indian population |

One more embodiment of the present invention relates to the novel gene variants wherein said variants are pharmacogenetic markers for predicting and detecting humans susceptible to asthma.

Another embodiment of the present invention relates to the R1 locus wherein percentage frequency of R1 locus dinucleotide on allele 16 is about 32% in the patients.

Still another embodiment of the present invention relates to the RI locus wherein percentage frequency of R1 locus dinucleotide on allele is about 30.67% in the patients.

Yet another embodiment of the present invention relates to the R3 wherein percentage frequency of R3 locus dinucleotide on allele 15 is about 35% in the patients.

One more embodiment of the present invention relates to the R3 locus, wherein the percentage frequency of R3 locus dinucleotide on allele 15 is about 32% in the patients.

The invention is illustrated by the following examples wherein the following samples are given by the way of illustration of the present invention and should not be construed to limit the scope of the present invention.

EXAMPLES

Example 1

II. Analysis of Polymorphisms

A. Preparation of Samples

Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed.

Many of the methods described below require amplification of DNA from target samples. This can be accomplished by e.g., PCR. See generally PCR Technology: Principles and Applications for DNA Amplification (ed. H. A. Erlich, Freeman Press, N.Y., N.Y., 1992); PCR Protocols: A Guide to Methods and Applications (eds. Innis, et al., Academic Press, San Diego, Calif., 1990); Mattila et al., Nucleic Acids Res. 19, 4967 (1991) and U.S. Pat. No. 4,683,202 (each of which is incorporated by reference for all purposes).

Other suitable amplification methods include the ligase chain reaction (LCR) (see Barringer K J et al, Gene 89:117-22, 1990; Friedhoff P et al, Anal Biochem 215:9-16, 1993) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Designing and synthesis of four new oligonucleotide primers (having sequence ID Nos. 3, 4, 5, 6 and 7) for PCR amplification of 392 bp region of STAT6 promoter region containing R1 polymorphism and 336 bp of the 5'-UTR (encoded in the exon 1) region containing R3 polymorphism of the human STAT6 gene. Here the Primers having SEQ ID Nos. 3, 4 and 7 were used in PCR amplification of 392 bp region of STAT-6 promoter region containing polymorphism at locus R1 region and primers having SEQ ID Nos. 5, 6 and 7 were used in PCR amplification of 336 region of 5'-UTR region containing polymorphisms at locus R3 region. The PCR amplification was conducted using 3-primers system in one reaction.

PCR amplification of genomic DNA samples isolated from peripheral blood leukocytes of the atopic asthmatic patients and normal control individuals using the above said primers. Genomic DNA was isolated from the peripheral blood of the patients and control individuals using a modified salting out procedure (Nagarkatti R et al., 2002). Briefly, 10 ml blood was obtained from patients and un-related control individuals using ACD Vaccutainers (BD Biosciences, San Jose, Calif., USA). Equal volume of ice cold C1 buffer (4×) was added and then 30 ml of ice cold sterile water was added to cause cell membrane lysis (Promega Genomic DNA Isolation Handbook). Following this, the nuclei were pelleted at 1300×g for 15 min at 4° C. The pellet was washed again with 1×C1 buffer. 12 ml of nuclear lysis buffer was added with 0.8 ml of 10% SDS. 50 µl of a 20 µg/µl solution of proteinase-K was added and the pellet resuspended by brief vortexing. After incubation at 65° C. for 2-3 hrs, the proteinaceous material was precipitated with the addition of 4 ml of 6M NaCl. After centrifugation for 15 min at 2500 rpm, the supernatant was transferred to another tube and two vol. of room temperature absolute ethanol was used to precipitate the DNA (Miller et al., 1988). The precipitated DNA was then washed with 70% ethanol twice, air-dried, and dissolved in TE buffer. Appropriate dilutions (1:100, in T.E buffer) were used to determine the OD at 260 nm and 280 nm. DNA quality was assessed using the 260 nm/280 nm ratio. The stock solution of the DNA was diluted to 50 ng/µl and used for PCR amplification and genotyping experiments. The stock DNA solution was stored at −20° C.

B. Detection of Polymorphisms in Target DNA

There are two distinct types of analysis depending whether a polymorphism in question has already been characterized. The first type of analysis is sometimes referred to as de novo characterization. This analysis compares target sequences in different individuals to identify points of variation, i.e., polymorphic sites. By analyzing a groups of individuals representing the greatest ethnic diversity among humans and greatest breed and species variety in plants and animals, patterns characteristic of the most common alleles/haplotypes of the locus can be identified, and the frequencies of such populations in the population determined. Additional allelic frequencies can be determined for subpopulations characterized by criteria such as geography, race, or gender. The de novo identification of the polymorphisms of the invention is described in the Examples section. The second type of analysis is determining which form(s) of a characterized polymorphism are present in individuals under test. There are a variety of suitable procedures, which are discussed in turn.

1. Repeat Detection (Size Variation Detection)

The design and use of primers flanking the sequence contain the repeat sequence or other polymorphic elements, which lead to a size difference. PCR amplification of the sequence leads to the presence of a pool of amplified products which differ by the specific repeat or polymorphism size. These size differences can then be detected using gel based, charge based methods. Usually for gel based detection one of the primers is labeled with a fluorescent compound which can then be excited and detected using a CCD camera or other methods.

2. Allele-Specific Probes

The design and use of allele-specific probes for analyzing polymorphisms is described by e.g., Saiki et al., Nature 324, 163-166, 1986; Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals.

3. Allele-Specific Primers

An allele-specific primer hybridizes to a site on target DNA overlapping a polymorphism and only primes amplification of an allelic form to which the primer exhibits perfect complementarily. This primer is used in conjunction with a second primer which hybridizes at a distal site. See, e.g., WO 93/22456.

4. Direct-Sequencing

The direct analysis of the sequence of polymorphisms of the present invention can be accomplished using either the dideoxy chain termination method or the Maxam Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

5. Tiling Arrays

The polymorphisms can also be identified by hybridization to nucleic acid arrays, some example of which are described by WO 95/11995 (incorporated by reference in its entirety for all purposes).

6. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR Technology, Principles and Applications for DNA Amplification, (W. H. Freeman and Co, New York, 1992), Chapter 7.

7. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., Proc. Nat. Acad. Sci. 86, 2766-2770, 1989. Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

III. Methods of Use

After determining polymorphic form(s) present in an individual at one or more polymorphic sites, this information can be used in a number of methods.

A. Correlation of Polymorphisms with Phenotypic Traits

Atopic diseases are heterogeneous in nature and as such there are many sub-phenotypes and traits to which the association can be observed. The polymorphisms of the invention may contribute to the phenotype of an organism in different ways. As described above the polymorphisms may act at various levels of cellular organization by which the disease phenotypes are observed as the end result. These polymorphisms may yield different selection advantages or disadvantages. For example, a heterozygous sickle cell mutation confers resistance to malaria, but a homozygous sickle cell mutation is usually lethal. A single polymorphism may affect more than one phenotypic trait.

Likewise, a single phenotypic trait may be affected by polymorphisms in different genes. Further, some polymorphisms predispose an individual to a distinct mutation that is causally related to a certain phenotype. Phenotypic traits include diseases that have known but hitherto unmapped genetic components. Phenotypic traits also include symptoms of, or susceptibility to, multifactorial diseases of which a component is or may be genetic, such as atopy, autoimmune diseases, inflammation, cancer, diseases of the nervous system, and infection by pathogenic microorganisms. Some examples of autoimmune diseases include systemic lupus erythematosus, rheumatoid arthritis, diabetes, multiple sclerosis, (insulin-dependent and non-independent), and Graves disease. Some examples of cancers include cancers of the breast, bladder, colon, brain, etc. As such, phenotypic traits also include characteristics, for example, susceptibility or receptivity to particular drugs or therapeutic treatments.

To perform association analysis of the disease phenotypes and genetic markers, the presence or absence of a set of polymorphisms (i.e. a polymorphic set) is determined for a set/population of the individuals, some of whom exhibit a particular trait termed variously as case/patients/affected/diseased individuals etc, and some of which exhibit lack of the trait termed variously as control individuals/normal etc. The alleles of each polymorphism of the set are then counted to determine if the presence or absence of a particular allele or a set of alleles or a haplotype is associated with the trait of interest. Test for such associations can be performed by standard statistical methods such as a $\chi 2$ test, Kolmogrov-Sirii-nov test, etc. Based on the values obtained for the hypothesis tested for example, the allele X is present more in patients then in controls and the allele X is not present more in patients than in controls, the significance value is obtained. If this value lies in a particular range then it determines the significance level of the correlations. For example, it might be found that the presence of allele A1 at polymorphic site 1 correlates with cystic fibrosis disease. As a further example, it might be found that the combined presence of allele A1 at polymorphic site 1 and allele B1 at polymorphic site 2 correlates with 10 fold-increased severity of cystic fibrosis.

Such associations can be of immediate benefit if an extremely strong correlation exists. For example, detection of cystic fibrosis polymorphism A1 and B1 in a patient may allow for rapid diagnosis and discrimination form other diseases which exhibit similar phenotypes; it can also allow for treatment if available; it can allow for screening of neonates for detection and/or for susceptibility and/or risk assessment; it can allow for selection of better and improved management methods for the disease from those which are available; it may allow for the treatment to be given if it is determined that the polymorphic site also correlates with particular therapeutic regimes and that such therapeutic drugs are more beneficial to the patient than other drugs.

B. Genetic Mapping of Phenotypic Traits

The previous section concerns identifying correlations between phenotypic traits and polymorphisms that directly or indirectly contribute to those traits. The present section describes identification of a physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. Please see (Altshuler D et al, 1998, N Engl J Med 338:1626; Cargill M et al, 1999, Nat Genet 22:231-8; Chang C, 1988, Proc Natl Acad Sci USA 85:6856-60; Hacia J G et al, 1999, Nat Genet 22:164-7; Hirschhorn J N et al, 2000, Proc Natl Acad Sci USA 97:12164-9; Lander E S and Botstein D, 1986, Proc Natl Acad Sci USA 83:7353-7; Lander E S, 1993, Nat Genet 4:5-6; Reich D E et al, 2001, Nature 411:199-204; Sachidanandam R et al, 2001, Nature 409:928-33. Genes localized by linkage can be cloned by a process known as directional cloning.

Computer programs are available for the calculation of lod scores for differing values of theta. Other references on linkage and disease mapping use above mentioned approaches include, Kreutz R et al, 1995, Proc Natl Acad Sci USA 92:8778-82; de Gouyon B et al, 1993, Proc Natl Acad Sci USA 90:1877-81; Julier C et al, 1990, Proc Natl Acad Sci USA 87:4585-9; Oberle I et al, 1986, Proc Natl Acad Sci USA 83:1016-20; Lathrop G M et al, 1984, Proc Natl Acad Sci USA 81:3443-6; Cohen D et al, 1984, Proc Natl Acad Sci USA 81:1774-8.

IV. Modified Polypeptides and Gene Sequences

The invention further provides variant forms of nucleic acids. The nucleic acids comprise at least ten contiguous bases of one of the sequences described in SEQ ID NO: 1. These variants can be used to identify the chromosomal backgrounds of individuals and depending on the particular haplotype risk may be assessed. The promoter polymorphism may also be important in the production of variant gene constructs containing the gene of interest so as to allow heterologous expression of the gene in various human and non-human cell lines. 5'-UTR polymorphism may lead to variant expression level changes due to transcriptional or post translational modifications.

Example 2

The invention further provides kits comprising at least one specific oligonucleotide labeled using fluorescent dyes as described above. For example, the same substrate can comprise allele-specific oligonucleotide probes for detecting at least 10, 100 or all of the polymorphisms listed. PCR cycling was carried out in a three-primer system in one reaction. Briefly, 0.01 μM to 0.05 μM M13T-FP was mixed with reverse primer (RP) and PCR amplified at the annealing temperature (Ta) for 25 cycles. Fluorescence labeling was done using M13-F primer and further cycling at 53.0° C., 8 cycles. PCR products were diluted in MilliQ water and 0.6 μl of the dilutions were mixed with loading buffer. The mix was treated at 94° C. for 2 minutes and loaded on a 6% polyacrylamide gel on a 377 ABI automated sequencer as per the manufacturers instructions (Applied Biosystems, Foster City, Calif., USA). Gels were analyzed using internal TAMRA labeled 550 base pair markers (Applied Biosystems, Foster City, Calif., USA). Repeat sizes were calculated using the formula n={(flanking region-allele size)/2, rounding off to 0 decimal values}. Optional additional components of the kit include, for example, restriction enzymes, reverse-transcriptase or polymerase, the substrate nucleoside triphosphates, means used to label (for example, an avidinenzyme conjugate and enzyme substrate and chromogen if the label is biotin), and the appropriate buffers for reverse transcription, PCR, or hybridization reactions. Usually, the kit also contains instructions for carrying out the methods.

Example 3

Direct sequencing of the purified PCR products using dye terminator chemistry on an ABI Prism 377 automated DNA sequencer. Sequencing was carried out using specific primers on an ABI 3100 capillary sequencer (Applied Biosystems, Foster City, Calif., USA) for a minimum of 20 atopic asthmatic and 20 control individuals. Nested primers were used for sequencing the entire PCR amplicons. PCR product was gel purified for sequencing. Briefly, sequencing primers, diluted to 1 pmole per μl, and 75-150 ng/μl PCR product were added to 5 μl reaction mix, and volume made up to 10 μl with autoclaved MilliQ water as per the Big Dye Terminator kit instructions (Applied Biosystems, Foster City, Calif., USA). PCR was set up with the following conditions: 96° C. for 5 seconds, 55° C. for 30 seconds and 60° C. for 4 minutes. Sequencing reactions were purified with 70% ethanol washes to remove unincorporated primers and fluorescent ddNTPs. Briefly, 26 μl autoclaved MilliQ water was added to the sequencing reaction. Sixty-four microliters of chilled 100% ethanol was added to the tubes and vortexed. The tubes were centrifuged at 16,000 g for 20 minutes at room temperature. Washes were performed with 70% ethanol by centrifugation at 16,000 g for 5 minutes. The pellets were air dried and resuspended in 10 μl of 100% Hi-Dye formamide. The tubes were incubated at 94° C. for 5 minutes and placed in the 3100 Automated Sequencer. Sequence analysis was carried out using Sequence Navigator (ver 2.1, Applied Biosystems, Foster City, Calif., USA) and DNAStar (ver 1.1, DNASTAR) software. Homozygous and heterozygous alleles were scored manually.

Aligning the above DNA sequences with the already existing sequence of human STAT6 gene for locating any sequence variations.

Designing of specific oligonucleotide probes for screening normal control individuals and the atopic asthmatic patients for novel single nucleotide polymorphisms.

Example 4

Calculating the frequency of di-nucleotide polymorphisms, R1 (Table 2) and R3 (Table 3), in normal individuals and atopic asthmatic patients for finding the association between these repeats and the disease. PCR cycling was carried out in a three-primer system in one reaction. Briefly, 0.01 μM to 0.05 μM M13T-FP was mixed with reverse primer (RP) and PCR amplified at the annealing temperature (Ta) for 25 cycles. Fluorescence labeling was done using M13-F primer and further cycling at 53.0° C., 8 cycles. PCR products were diluted in MilliQ water and 0.6 μl of the dilutions were mixed with loading buffer. The mix was treated at 94° C. for 2 minutes and loaded on a 6% polyacrylamide gel on a 377 ABI automated sequencer as per the manufacturers instructions (Applied Biosystems, Foster City, Calif., USA). Gels were analyzed using internal TAMRA labeled 550 base pair markers (Applied Biosystems, Foster City, Calif., USA). Repeat sizes were calculated using the formula n={(flanking region-allele size)/2, rounding off to 0 decimal values}.

TABLE 2

Frequency (%) of R1 dinucleotide repeats in patients and controls.

| S. No. | Allele | Patient (%) | Control (%) |
|---|---|---|---|
| 1 | 11 | 0.44 | 0.23 |
| 2 | 12 | 0 | 0.23 |
| 3 | 13 | 0.22 | 0.47 |
| 4 | 14 | 0.22 | 0.47 |
| 5 | 15 | 0.22 | 1.64 |
| 6 | 16 | 30.67 | 23.00 |
| 7 | 17 | 8.44 | 9.39 |
| 8 | 18 | 0.89 | 1.64 |
| 9 | 19 | 2 | 3.05 |
| 10 | 20 | 1.33 | 1.17 |
| 11 | 21 | 2.22 | 0.94 |
| 12 | 22 | 6.89 | 6.81 |
| 13 | 23 | 17.56 | 17.37 |
| 14 | 24 | 16.22 | 21.83 |
| 15 | 25 | 6.22 | 7.04 |
| 16 | 26 | 3.78 | 2.35 |
| 17 | 27 | 1.33 | 0.70 |
| 18 | 28 | 0.67 | 1.17 |
| 19 | 29 | 0.22 | 0 |
| 20 | 31 | 0.22 | 0 |
| 21 | 32 | 0.22 | 0.47 |

Estimating the frequencies of haplotypes generated using the R1 and R3 polymorphisms in the normal individuals and atopic asthmatic patients for finding association between these haplotypes and the disease (Table 4). Kolmogrov-Smrinov test was used to test for allelic association with disease at R1 and R3 loci (225 patients, 212 controls). Initial test for association between the R1 and R3 loci, stratified by phenotype (case, control) was done using Cochran-Mantel-Haenszel test. Haplotypes were generated using the PHASE program (30) for the patient (N=225) and control (N=212) groups. Default parameters were used to generate the haplotypes. No missing values were allowed (http://archimedes.well.ox.ac.uk/pise/PHASE-simple.html, PHASE Ver. 2.0.2). Odds ratios were calculated and Chi-square test for association with phenotype, was carried out.

TABLE 3

Frequency (%) of R3 dinucleotide repeats in patients and controls.

| S. No. | Allele | Patient (%) | Control (%) |
|---|---|---|---|
| 1 | 13 | 0 | 1.42 |
| 2 | 14 | 8.67 | 11.32 |
| 3 | 15 | 34 | 19.34 |
| 4 | 16 | 7.78 | 20.52 |
| 5 | 17 | 41.56 | 39.62 |
| 6 | 18 | 5.11 | 5.42 |
| 7 | 19 | 1.33 | 1.42 |
| 8 | 20 | 0.44 | 0.94 |
| 9 | 22 | 0.67 | 0 |
| 10 | 24 | 0.44 | 0 |

The repeats have been denoted with the allele size (16, 17, etc), the genotypes with (16/17), and the haplotypes with (R1_R3 or 16__17).

Other and further aspects, features, and advantages of the present invention will be apparent from the following description of the presently preferred embodiments of the invention given for the purpose of disclosure.

Figure 1:
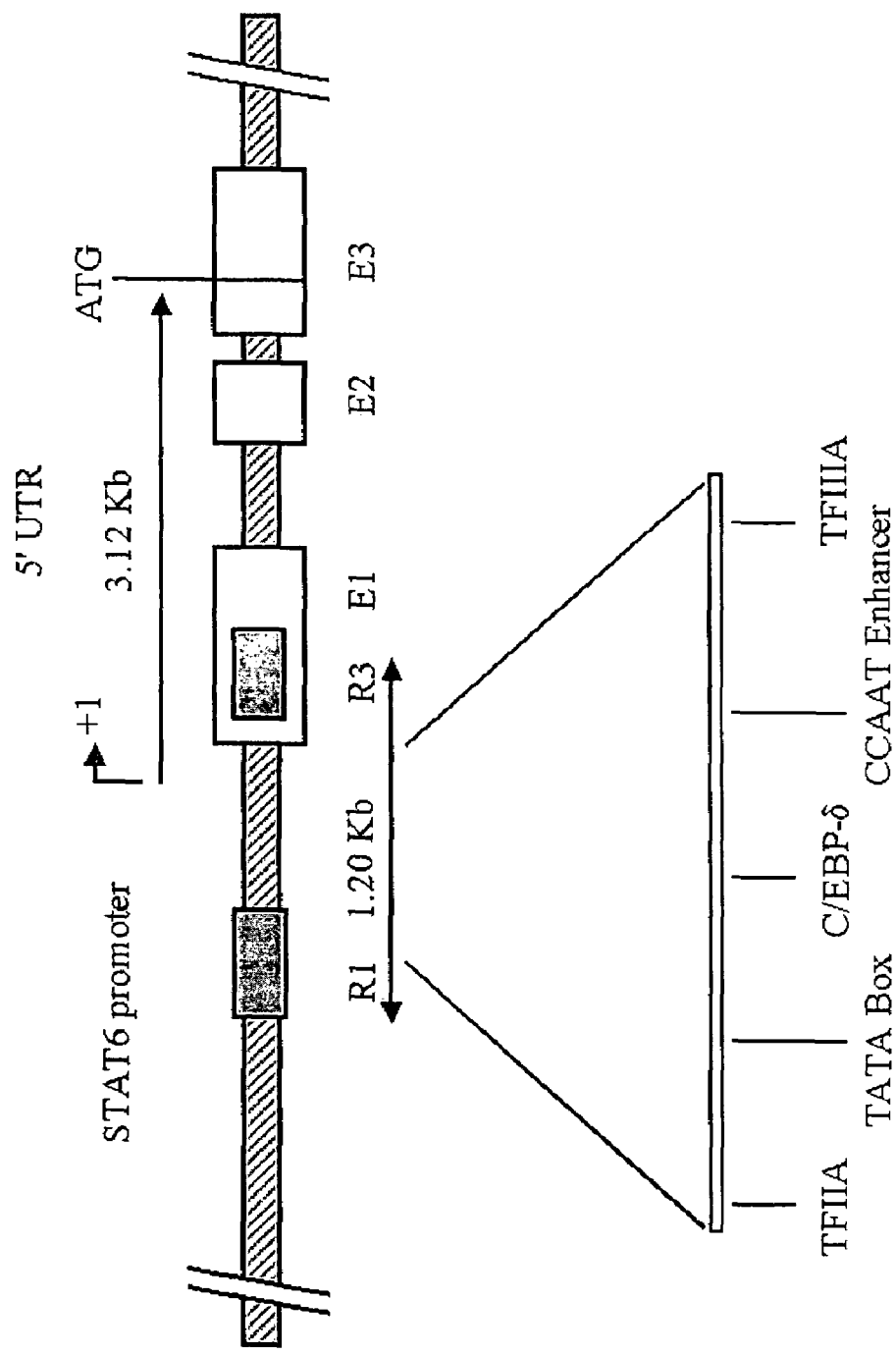

The present application provides one di-nucleotide polymorphic repeat at nucleotide 1032 to 1075 in the promoter region of the human STAT6 gene sequence (GenBank accession no. AH006951). The first polymorphic site (R1), as shown in FIG. 1, is 5660 bp upstream of the ATG site. The second polymorphic site (R3) is situated 3691 to 3732 nucleotides of the human STAT6 gene sequence (GenBank accession no. AH006951). R3 polymorphic site is 3003 bp upstream of the ATG site (as shown in FIG. 1)

TABLE 4

Frequency (%) of R1__R3 Haplotypes in patients and controls estimated by PHASE. Haplotypes with relative frequencies > 0.025 (2.5% of sample size) in either of the groups have been depicted below:

| S. No. | Haplotype | Patient (%) | Control (%) |
|---|---|---|---|
| 1 | 16_14 | 4.7 | 4 |
| 2 | 16_15 | 18.7 | 10.8 |
| 3 | 16_16 | 0.9 | 1.7 |
| 4 | 16_17 | 6.2 | 5 |
| 5 | 17_14 | 0.4 | 4.2 |
| 6 | 17_15 | 7.1 | 2.8 |
| 7 | 17_16 | 0.2 | 1.2 |
| 8 | 18_17 | 0 | 1.2 |
| 9 | 21_17 | 1.1 | 0.2 |
| 10 | 22_16 | 1.3 | 1.4 |
| 11 | 22_17 | 4.7 | 5 |
| 12 | 23_14 | 1.6 | 0.5 |
| 13 | 23_15 | 1.6 | 2.4 |
| 14 | 23_16 | 0.4 | 4.7 |
| 15 | 23_17 | 11.1 | 9 |
| 16 | 23_18 | 2 | 0.2 |
| 17 | 24_15 | 2.7 | 0.5 |
| 18 | 24_16 | 0.7 | 7.1 |
| 19 | 24_17 | 10.2 | 11.1 |
| 20 | 24_18 | 1.8 | 2.6 |
| 21 | 25_16 | 0.9 | 2.6 |
| 22 | 25_17 | 4.7 | 2.1 |
| 23 | 26_15 | 1.1 | 0 |
| 24 | 26_16 | 1.3 | 0.2 |
| 25 | 26_17 | 0.4 | 1.9 |

So the matter in which the above mentioned features, advantages and the objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and thereof not to be considered limiting in their scope. n general, the frequencies have been plotted on the Y axis as a percentage for the particular chromosomes or haplotypes.

Figure 2:
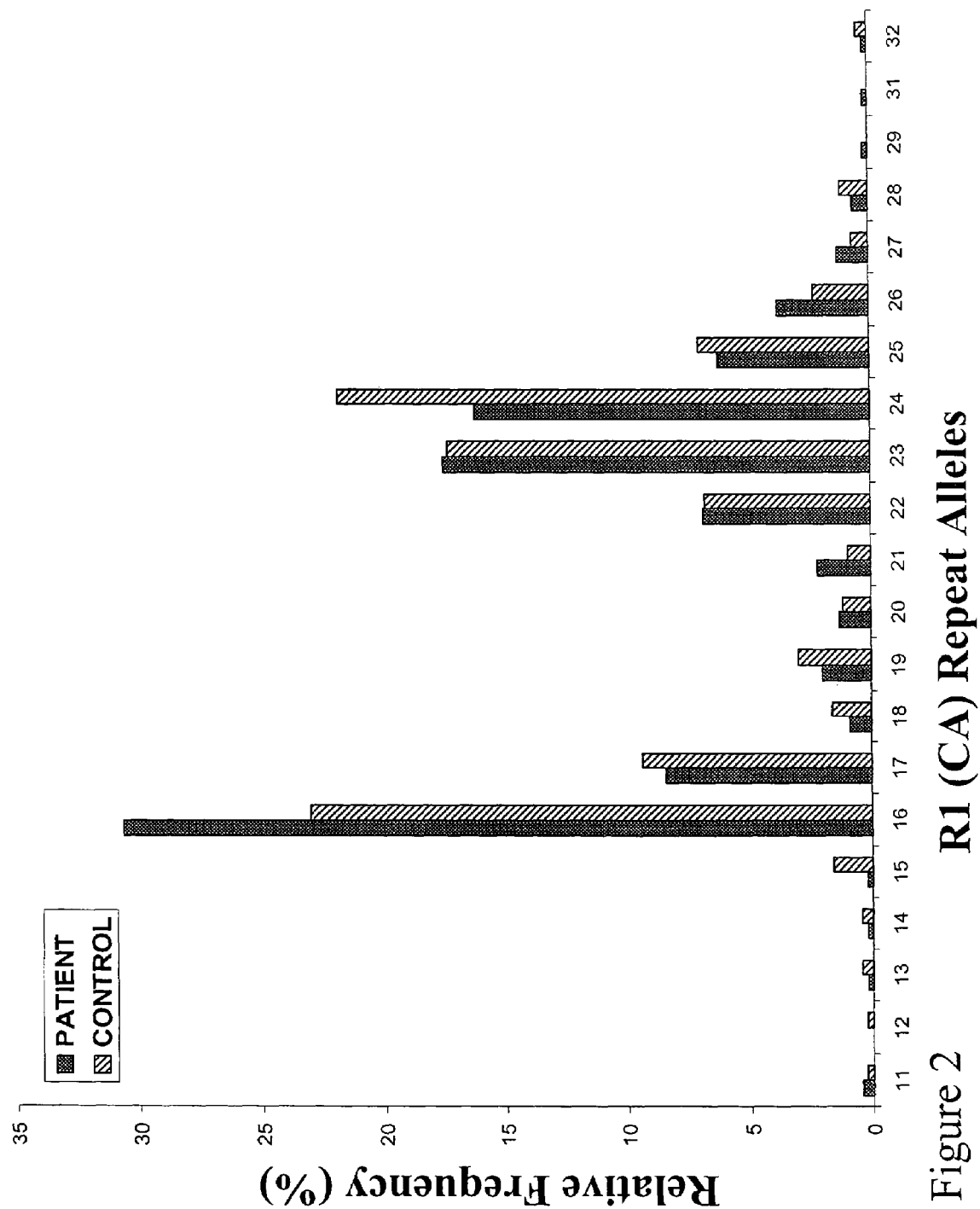
FIG. 2 shows the distribution of R1 di-nucleotide alleles in 426 normal chromosomes and 450 asthmatic patient chromosomes (Table 1). The figure depicts the allele frequencies at the R1 locus with the repeat sizes depicted on the X-axis and their respective frequencies on the Y-axis.

To demonstrate the association of the R1 repeat locus with atopic disorders such as asthma, Kolmogrov-Smirnov test was performed (Nagarkatti et al., 2000; Carriere Kochar 2000, Mukawa et. al., 1989). The Kolmogrov-Smirnov Test is a non-metric test which gives the likelihood of two ordered categorizations coming from different orderings or the same ordering. The Kolmogrov-Smirnov test (KS-tries to determine if two datasets differ significantly. The KS-test has the advantage of being more powerful than the chi-square test in many situations. This analysis showed significant differences between the allele count distribution of patient and control groups (p=0.24). It was observed an inversion in major and minor modes between the controls (major 24 repeat and minor 16 repeat) and patients (major 16 repeats and minor 24 repeats). The difference between patients and controls for the 16 allele was found to be significant (OR=1.48, 95% CI= (1.09, 2.00) but 99% CI=(0.99, 2.20); LR $\chi2$=6.56, p=0.01) (FIG. 2, Table 1). However, the difference in the overall distribution of alleles in patients and controls was not found to be statistically significant (KS $\chi2$=2.87, df=2, p=0.24) (FIG. 2). One-way ANOVA showed an association between the alleles at this locus and log total serum IgE levels in the patients {F=2.65, df=(12, 221), p=0.002}. Tukey-Kramer HSD (Honestly Significant Difference) showed significant difference between mean log IgE levels for the pairs of alleles: 16 and 25, 22 and 26, 22 and 25. At the genotype level, 16/23 was found to be associated with phenotype with an odds ratio of 2.20 and Wald's 95% CI (1.13, 4.25) (but 99% CI=(0.91, 5.23)). However, none of the genotypes at the R1 locus was associated with log total serum IgE levels (F=1.20, df=(32, 110), p=0.26).

Example 5

Figure 3:
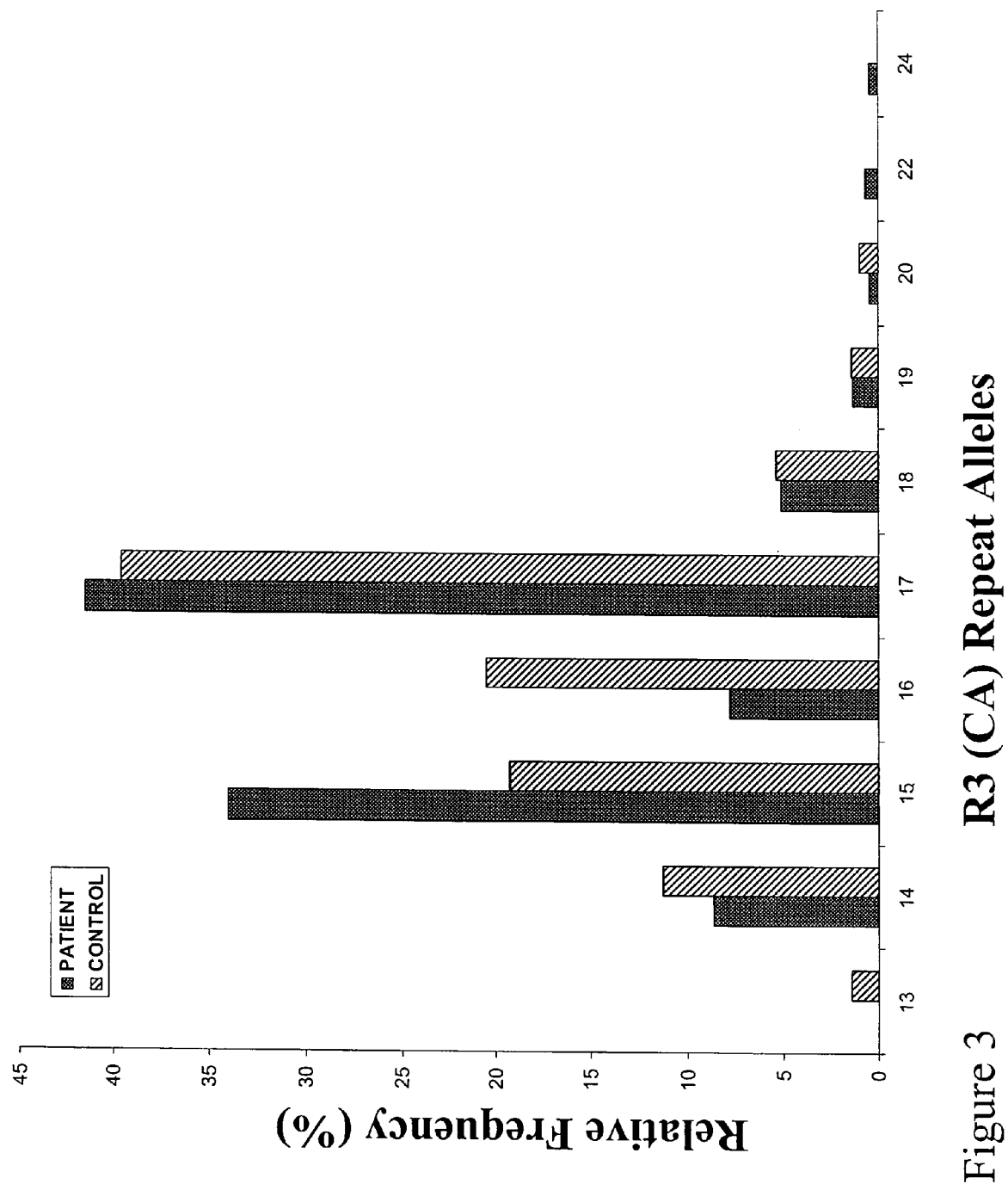
FIG. 3 shows the distribution of R3 di-nucleotide alleles in 426 normal chromosomes and 450 asthmatic patient chromosomes (Table 2). The figure depicts the allele frequencies at the R3 locus with the repeat sizes depicted on the X-axis and their respective frequencies on the Y-axis.

To demonstrate the association of the R3 repeat locus, KS test was performed. A significant difference in the allele count distribution was observed between control and patient groups (KS $\chi^2$=0.01, df=2, p=0.007). An examination of allele counts showed that the largest difference between patients and controls was for the 15 and 16 repeat alleles, respectively (FIG. 3, Table 2). The largest difference in the cumulative frequencies was for the 15 repeat allele (0.105). The odds ratio for patients having 15 repeats rather than any other allele, as compared to controls is 1.76 with Wald's 99% CI=(1.18, 2.60); LR $\chi^2$=4.10, p<0.0001). On the other hand, the 16 repeat allele was found to be associated with controls with odds ratio 0.33 and 99% CI=(0.19, 0.57). Further, the 15/17 R3 genotype was found to be over-represented in the patient group as compared to the control group (relative frequency, 0.37 vs 0.15). The odds ratio for patients having 15/17 genotype as compared to controls was 3.42 with Wald's 99% CI=(1.90, 6.30); LR $\chi^2$=29.53, p<0.0001). Hence, the R3 repeat locus is strongly associated with asthma. However, no association was found between the alleles or genotypes at R3 locus with log total serum IgE levels {F=0.23, df=(16, 110), p=1.00) (as shown in FIG. 3 and Table 2)

Example 6

To demonstrate the association of the two repeat with the atopic phenotype for example asthma, the inventors have also carried out Cochran-Mantel-Haenzel test (Piacquadio et. al, 2004, Christie et. al, 2002, Sorensen et. al, 2002, Longo et. al, 2001) for R3 by R1, stratified by phenotype and found general association of categories (p<0.0001, $\chi^2$=1976.45, df=1587). The CMH test allows one to use sample sets containing less than five counts per cell and is more powerful than the chi-square test for association. The repeat data and other polymorphism data can be considered to be of nominal or ordinal type and therefore this test can be utilized. Furthermore the test allows three-way analysis to be performed, thereby avoiding the problem of loss of significance due to multiple testing. This suggested that there was some kind of association between the R1 and R3 loci for at least one stratum (i.e. patients and controls separately).

A programme by name of PHASE program was used to generate haplotypes for the patient and control groups. The program PHASE implements a new statistical method for reconstructing haplotypes from population genotype data. Experiments with the software on both real and simulated data indicate that it can provide an improvement on the EM algorithm for reconstructing haplotypes. It allows for missing genotype data and also can handle more than one locus irrespective of the polymorphism, for example SNP and repeats can be analyzed simultaneously. Based on the output from the software the probability values of the haplotypes are also predicted and can be utilized to differentiate more confident haplotypes. The PHASE software is suitable for genetic distances of 100 cM or less and these two polymorphism are in a range of approximately 0.1 cM. The probability values for the chromosomes with uncertain phase ranged form 0.51 to 0.65 for both the groups; these chromosomes accounted for only 2.07% of the control and 2.60% of the patient chromosomes. The haplotypes whose expected frequency was larger than 0.025, in either of the two groups are shown in Table 3 (FIG. 4). The odds in favor of patients rather than controls having 17_15 and 16_15 haplotypes were 2.63 with 99% CI=(1.08, 6.40) and 1.89 with 99% CI=(1.13, 3.13), respectively. The corresponding likelihood ratio $\chi^2$ tests showed p-value less than 0.0031 and 0.001, respectively, which continue to be significant at 5% level after Bonferroni correction. Thus the 2-locus haplotypes, 17_15 and 16_15, were strongly associated with asthma. On the other hand, the odds in favor of patients rather than controls having 17_14, 23_16 and 24_16 haplotypes were 0.10 with 99% CI=(0.01, 0.69), 0.09 with 99% CI=(0.01, 0.61) and 0.09 with 99% CI=(0.02, 0.42), respectively. The corresponding likelihood chi-square tests showed p-values less than 0.00001 for all the three haplotypes, which were significant after Bonferroni correction. (as shown in FIG. 4). This example is important to complete the nature of present invention which has not been addressed nor shown in the earlier studies.

The novelty of the present invention is linked with findings that the haplotypes 17_14, 23_16 and 24_16, have been identified to be linked with protection of asthma. In the other words, the identifications and disclosure of the haplotypes responsible for protection from asthma was of particular importance. This enables a comparative analysis between the asthmatics and non-asthmatics and the relationship of various haplotypes which govern the nature of said disease. This fact is unique in itself and holds against all known prior studies wherein such facts were never considered nor studied. The understanding of such analysis will enable early detection in patients. This will guide the medical practitioners for better and improved treatment and development of efficient drugs.

REFERENCES

1. Abney M, Ober C, McPeek M S (2002) Quantitative-trait homozygosity and association mapping and empirical genomewide significance in large, complex pedigrees: fasting serum-insulin level in the Hutterites. Am J Hum Genet 70:920-34.
2. Arinobu Y, Sugimoto R, Akaiwa M, Arima K, Otsuka T, Hamasaki N, Izuhara K (2000) Augmentation of signal transducer and activation of transcription (STAT)6 and STAT3 expression in stimulated B and T cells. Biochem Biophys Res Commun 277:317-24.
3. Akimoto T, Numata F, Tamura M, Takata Y, Higashida N, Takashi T, Takeda K, et al (1998) Abrogation of bronchial eosinophilic inflammation and airway hyperreactivity in signal transducers and activators of transcription (STAT6) 6-deficient mice. J Exp Med 187:1537-42.
4. Altshuler D, Kruglyak L, Lander E (1998) Genetic polymorphisms and disease. N Engl J Med 338:1626.
5. Babron M C, Selinger-Leneman H, Dizier M H, Clerget-Darpoux F (2001) Homogeneity of asthma genome scan results. Genet Epidemiol 21 Suppl 1:S44-8.
6. Barringer K J, Orgel L, Wahl G, Gingeras T R (1990) Blunt-end and single-strand ligations by *Escherichia coli* ligase: influence on an in vitro amplification scheme. Gene 89:117-22
7. Baron M (2001) The search for complex disease genes: fault by linkage or fault by association? Mol Psychiatry 6:143-9.
8. Barnes P J (2001) Th2 cytokines and asthma: an introduction. Respir Res 2:64-5.
9. Barnes K C (1999) Gene-environment and gene-gene interaction studies in the molecular genetic analysis of asthma and atopy. Clin Exp Allergy 29 Suppl 4:47-51.
10. Barnes K C, Neely J D, Duffy D L, Freidhoff L R, Breazeale D R, Schou C, Naidu R P, et al (1996) Linkage of asthma and total serum IgE concentration to markers on chromosome 12q: evidence from Afro-Caribbean and Caucasian populations. Genomics 37:41-50.
11. Ben-Asouli Y, Banai Y, Pel-Or Y, Shir A, Kaempfer R (2002) Human interferon-gamma mRNA autoregulates its translation through a pseudoknot that activates the interferon-inducible protein kinase PKR. Cell 108:221-32
12. Bhattacharyya S, Leaves N I, Wiltshire S, Cox R, Cookson W O (2000) A high-density genetic map of the chromosome 13q14 atopy locus. Genomics 70:286-91.
13. Bleecker E R, Postma D S, Meyers D A (1997) Evidence for multiple genetic susceptibility loci for asthma. Am J Respir Crit Care Med 156:S113-6.

14. Blumenthal M N, Amos D B (1987) Genetic and immunologic basis of atopic responses. Chest 91:176S-184S.
15. Bodmer W F (1987) The human genome sequence and the analysis of multifactorial traits. Ciba Found Symp 130:215-28.
16. Breslow J L (1988) Apolipoprotein genetic variation and human disease. Physiol Rev 68:85-132.
17. Caraballo L R, Hernandez M (1990) HLA haplotype segregation in families with allergic asthma. Tissue Antigens 35:182-6.
18. Cargill M, Altshuler D, Ireland J, Sklar P, Ardlie K, Patil N, Shaw N, et al (1999) Characterization of single-nucleotide polymorphisms in coding regions of human genes. Nat Genet 22:231-8.
19. Carriere K C, Kochar S C (2000): Comparing sub-survival functions in a competing risks model. Lifetime Data Anal.: 6(1):85-97.
20. Chang C, Bowman J L, DeJohn A W, Lander E S, Meyerowitz E M (1988) Restriction fragment length polymorphism linkage map for *Arabidopsis thaliana*. Proc Natl Acad Sci USA 85:6856-60.
21. Christie L, Hine R J, Parker J G, Burks W (2002). Food allergies in children affect nutrient intake and growth. J Am Diet Assoc. 102 (11):1648-51
22. Cohen D, Cohen O, Marcadet A, Massart C, Lathrop M, Deschamps I, Hors J, et al (1984) Class II HLA-DC beta-chain DNA restriction fragments differentiate among HLA-DR2 individuals in insulin-dependent diabetes and multiple sclerosis. Proc Natl Acad Sci USA 81:1774-8.
23. Cookson W O, Young R P, Sandford A J, Moffatt M F, Shirakawa T, Sharp P A, Faux J A, et al (1992) Maternal inheritance of atopic IgE responsiveness on chromosome 11q. Lancet 340:381-4.
24. Cookson W (1999) The alliance of genes and environment in asthma and allergy. Nature 402:B5-11.
25. Duetsch G, Illig T, Loesgen S, Rohde K, Klopp N, Herbon N, Gohlke H, et al (2002) STAT6 as an asthma candidate gene: polymorphism-screening, association and haplotype analysis in a Caucasian sib-pair study. Hum Mol Genet 11:613-21.
26. Duffy D L (1997) Genetic epidemiology of asthma. Epidemiol Rev 19:129-43.
27. Erlich H A (eds), Freeman Press, N.Y., N.Y., 1992); PCR Protocols: A Guide to Methods and Applications (eds. Innis, et al., Academic Press, San Diego, Calif., 1990.
28. Friedhoff P, Hahn M, Wolfes H, Pingoud A (1993) Quantitative polymerase chain reaction with oligodeoxynucleotide ligation assay/enzyme-linked immunosorbent assay detection. Anal Biochem 215:9-16.
29. Finkelman F D, Morris S C, Orekhova T, Mori M, Donaldson D, Reiner S L, Reilly N L, et al (2000) Stat6 regulation of in vivo IL-4 responses. J Immunol 164:2303-10.
30. de Gouyon B, Melanitou E, Richard M F, Requarth M, Hahn I H, Guenet J L, Demenais F, et al (1993) Genetic analysis of diabetes and insulitis in an interspecific cross of the nonobese diabetic mouse with *Mus spretus*. Proc Natl Acad Sci USA 90:1877-81.
31. Gao P S, Mao X Q, Roberts M H, Arinobu Y, Akaiwa M, Enomoto T, Dake Y, et al (2000) Variants of STAT6 (signal transducer and activator of transcription 6) in atopic asthma. J Med Genet 37:380-2.
32. Gebhardt F, Zanker K S, Brandt B (1999) Modulation of epidermal growth factor receptor gene transcription by a polymorphic dinucleotide repeat in intron 1. J Biol Chem 274:13176-80.
33. Hacia J G, Fan J B, Ryder O, Jin L, Edgemon K, Ghandour G, Mayer R A, et al (1999) Determination of ancestral alleles for human single-nucleotide polymorphisms using high-density oligonucleotide arrays. Nat Genet 22:164-7.
34. Heinzmann A, Grotherr P, Jerkic S P, Lichtenberg A, Braun S, Kruse S, Forster J, et al (2000) Studies on linkage and association of atopy with the chromosomal region 12q13-24. Clin Exp Allergy 30:1555-61.
35. Hill S, Herlaar E, Le Cardinal A, van Heeke G, Nicklin P (1999) Homologous human and murine antisense oligonucleotides targeting stat6. Functional effects on germline cepsilon transcript. Am J Respir Cell Mol Biol 21:728-37.
36. Hirschhorn J N, Sklar P, Lindblad-Toh K, Lim Y M, Ruiz-Gutierrez M, Bolk S, Langhorst B, et al (2000) SBE-TAGS: an array-based method for efficient single-nucleotide polymorphism genotyping. Proc Natl Acad Sci USA 97:12164-9.
37. Horvath C M (2000) STAT proteins and transcriptional responses to extracellular signals. Trends Biochem Sci 25:496-502.
38. Ihle J N (2001) The Stat family in cytokine signaling. Curr Opin Cell Biol 13:211-7.
39. Julier C, de Gouyon B, Georges M, Guenet J L, Nakamura Y, Avner P, Lathrop G M (1990) Minisatellite linkage maps in the mouse by cross-hybridization with human probes containing tandem repeats. Proc Natl Acad Sci USA 87:4585-9.
40. Kreutz R, Hubner N, James M R, Bihoreau M T, Gauguier D, Lathrop G M, Ganten D, et al (1995) Dissection of a quantitative trait locus for genetic hypertension on rat chromosome 10. Proc Natl Acad Sci USA 92:8778-82.
41. Kwoh D Y, Davis G R, Whitfield K M, Chappelle H L, DiMichele L J, Gingeras T R (1989) Transcription-based amplification system and detection of amplified human immunodeficiency virus type 1 with a bead-based sandwich hybridization format. Proc Natl Acad Sci USA 86:1173-7.
42. Lander E S, Botstein D (1986) Strategies for studying heterogeneous genetic traits in humans by using a linkage map of restriction fragment length polymorphisms. Proc Natl Acad Sci USA 83:7353-7.
43. Lander E S (1993) Finding similarities and differences among genomes. Nat Genet 4:5-6.
44. Lathrop G M, Lalouel J M, Julier C, Ott J (1984) Strategies for multilocus linkage analysis in humans. Proc Natl Acad Sci USA 81:3443-6.
45. Levitt R C (1994) Molecular genetic methods for mapping disease genes. Am J Respir Crit Care Med 150:S94-9.
46. Linehan L A, Warren W D, Thompson P A, Grusby M J, Berton M T (1998) STAT6 is required for IL-4-induced germline Ig gene transcription and switch recombination. J Immunol 161:302-10.
47. Longo D R, Johnson J C, Kruse R L, Brownson R C, Hewett J E (2001): A prospective investigation of the impact of smoking bans on tobacco cessation and relapse. Tob Control, September; 10(3):267-72.
48. Mathew A, MacLean J A, DeHaan E, Táger A M, Green F H, Luster A D (2001) Signal transducer and activator of transcription 6 controls chemokine production and T helper cell type 2 cell trafficking in allergic pulmonary inflammation. J Exp Med 193:1087-96.
49. Mattila P, Korpela J, Tenkanen T, Pitkanen K (1991) Fidelity of DNA synthesis by the *Thermococcus litoralis* DNA polymerase—an extremely heat stable enzyme with proofreading activity. Nucleic Acids Res 19:4967-73.
50. Miyata S, Matsuyama T, Kodama T, Nishioka Y, Kuribayashi K, Takeda K, Akira S, et al (1999) STAT6 deficiency in a mouse model of allergen-induced airways inflammation abolishes eosinophilia but induces infiltration of CD8+ T cells. Clin Exp Allergy 29:114-23.
51. Mokdad-Gargouri R, Belhadj K, Gargouri A (2001) Translational control of human p53 expression in yeast mediated by 5'-UTR-ORF structural interaction. Nucleic Acids Res 29:1222-7.
52. Mukawa A, Kamitsuma Y, Tsunekawa S, Tanaka N (1989): Report on a long-term trial of CYBEST Model 2 for prescreening for squamous cell carcinoma of the uterine cervix Anal Cell Pathol. August; 1(4):225-33.
53. Mullings R E, Wilson S J, Puddicombe S M, Lordan J L, Bucchieri F, Djukanovic R, Howarth P H, et al (2001) Signal transducer and activator of transcription 6 (STAT-6) expression and function in asthmatic bronchial epithelium. J Allergy Clin Immunol 108:832-8. Nelms K, Keegan A D, Zamorano J, Ryan J J, Paul W E (1999) The IL-4 receptor: signaling mechanisms and biologic functions: Annu Rev Immunol 17:701-38.
54. Ober C, Tsalenko A, Parry R, Cox N J (2000) A second-generation genomewide screen for asthma-susceptibility alleles in a founder population. Am J Hum Genet 67:1154-62.
55. Oberle I, Heilig R, Moisan J P, Kloepfer C, Mattei G M, Mattei J F, Boue J, et al (1986) Genetic analysis of the fragile-X mental retardation syndrome with two flanking polymorphic DNA markers. Proc Natl Acad Sci USA 83:1016-20.
56. Orita M, Iwahana H, Kanazawa H, Hayashi K, Sekiya T (1989) Detection of polymorphisms of human DNA by gel electrophoresis as single-strand conformation polymorphisms. Proc Natl Acad Sci USA 86:2766-70.
57. Patel B K, Keck C L, O'Leary R S, Popescu N C, LaRochelle W J (1998) Localization of the human stat6 gene to chromosome 12q13.3-q14.1, a region implicated in multiple solid tumors. Genomics 52:192-200.
58. Paul W E (1997) Interleukin 4: signalling mechanisms and control of T cell differentiation. Ciba Found Symp 204:208-16; discussion 216-9.
59. Piacquadio D J, Chen D M, Farber H F, Fowler J F Jr, Glazer S D, Goodman J J, Hruza L L, Jeffes E W, Ling M R, Phillips T J, Rallis T M, Scher R K, Taylor C R, Weinstein G D (2004): Photodynamic therapy with aminolevulinic acid topical solution and visible blue light in the treatment of multiple actinic keratoses of the face and scalp: investigator-blinded, phase 3, multicenter trials. Arch Dermatol.; 140(1): 41-6.
60. Reich D E, Cargill M, Bolk S, Ireland J, Sabeti P C, Richter D J, Lavery T, et al (2001) Linkage disequilibrium in the human genome. Nature 411:199-204.
61. Rothenburg S, Koch-Nolte F, Rich A, Haag F (2001) A polymorphic dinucleotide repeat in the rat nucleolin gene forms Z-DNA and inhibits promoter activity. Proc Natl Acad Sci USA 98:8985-90.
62. Sachidanandam R. Weissman D, Schmidt S C, Kakol J M, Stein L D, Marth G, Sherry S, et al (2001) A map of human genome sequence variation containing 1.42 million single nucleotide polymorphisms. Nature 409:928-33.
63. Sambrook et al., Molecular Cloning, A Laboratory Manual, 2nd Ed., CSHP, New York 1989.
64. Saiki R K, Bugawan T L, Horn G T, Mullis K B, Erlich H A (1986) Analysis of enzymatically amplified beta-globin and HLA-DQ alpha DNA with allele-specific oligonucleotide probes. Nature 324:163-6.
65. Sherman M A, Secor V H, Brown M A (1999) IL-4 preferentially activates a novel STAT6 isoform in mast cells. J Immunol 162:2703-8.
66. Sorensen G, Emmons K, Stoddard A M, Linnan L, Avrunin J (2002): Do social influences contribute to occupational differences in quitting smoking and attitudes toward quitting? Am J Health Promot. January-February; 16(3): 135-41.
67. Stephens M, Smith N J, Donnelly P (2001) A new statistical method for haplotype reconstruction from population data. Am J Hum Genet 68:978-89.
68. Tamura K, Arakawa H, Suzuki M, Kobayashi Y, Mochizuki H, Kato M, Tokuyama K, et al (2001) Novel dinucleotide repeat polymorphism in the first exon of the STAT-6 gene is associated with allergic diseases. Clin Exp Allergy 31:1509-14.
69. Takeda K, Akira S (2000) STAT family of transcription factors in cytokine-mediated biological responses. Cytokine Growth Factor Rev 11:199-207.
70. Tay A H, Tan E C, Chew F T, Goh D L, Shek L P, Lee B W (1999) Ethnic differences in genetic susceptibility to atopy and asthma. Asian Pac J Allergy Immunol 17:239-42.
71. Thomas N S, Wilkinson J, Holgate S T (1997) The candidate region approach to the genetics of asthma and allergy. Am J Respir Crit Care Med 156:S144-51.
72. Tomkinson A, Kanehiro A, Rabinovitch N, Joetham A, Cieslewicz G, Gelfand E W (1999) The failure of STAT6-deficient mice to develop airway eosinophilia and airway hyperresponsiveness is overcome by interleukin-5. Am J Respir Crit Care Med 160:1283-91.
73. Yagi R, Nagai H, Iigo Y, Akimoto T, Arai T, Kubo M (2002) Development of atopic dermatitis-like skin lesions in STAT6-deficient NC/Nga mice. J Immunol 168:2020-7.
74. Yang M, Hogan S P, Henry P J, Matthaei K I, McKenzie A N, Young I G, Rothenberg M E, et al (2001) Interleukin-13 mediates airways hyperreactivity through the IL-4 receptor-alpha chain and STAT-6 independently of IL-5 and eotaxin. Am J Respir Cell Mol Biol 25:522-30.
75. Yokozeki H, Ghoreishi M, Takagawa S, Takayama K, Satoh T, Katayama I, Takeda K, et al (2000) Signal transducer and activator of transcription 6 is essential in the induction of contact hypersensitivity. J Exp Med 191:995-1004.
76. Xu J, Wiesch D G, Meyers D A (1998) Genetics of complex human diseases: genome screening, association studies and fine mapping. Clin Exp Allergy 28 Suppl 5:1-5; discussion 26-8.
77. Xu J, Meyers D A, Ober C, Blumenthal M N, Mellen B, Barnes K C, King R A, et al (2001) Genomewide screen and identification of gene-gene interactions for asthma-susceptibility loci in three U.S. populations: collaborative study on the genetics of asthma. Am J Hum Genet 68:1437-46.
78. Zhang S, Lukacs N W, Lawless V A, Kunkel S L, Kaplan M H (2000) Cutting edge: differential expression of chemokines in Th1 and Th2 cells is dependent on Stat6 but not Stat4. J Immunol 165:10-4.
79. Zhu J, Guo L, Watson C J, Hu-Li J, Paul W E (2001) Stat6 is necessary and sufficient for IL-4's role in Th2 differentiation and cell expansion. J Immunol 166:7276-81.
80. Zyskind et al., Recombinant DNA Laboratory Manual, (Acad. Press, 1988).
81. U.S. Pat. No. 4,683,202
82. WO 93/22456
83. WO 89/11548
84. WO 95/11995

We claim:

1. An isolated allelic variant consisting of R1 and R3 loci, wherein said R1 locus consists of GT dinucleotide repeats from nucleotide position 125 from the 5' end of SEQ ID NO:1 and said R3 locus consists of GT dinucleotide repeats from nucleotide position 87 from the 5' end of SEQ ID NO:2 of Signal Transducer and Activator of Transcription-6 (STAT-6) gene for use in predicting susceptibility of a human subject to atopic asthma,
   wherein the isolated variants have haplotype 17_15, where the haplotype has 17 repeats on the R1 locus and 15 repeats on R3 locus, and
   wherein the isolated variants have haplotype 16_15, where the haplotype has 16 repeats on the R1 locus and 15 repeats on the R3 locus, and
   wherein these haplotypes are associated with susceptibility to asthma.

2. An isolated allelic variant consisting of R1 and R3 loci, wherein said R1 locus consists of GT dinucleotide repeats from nucleotide position 125 from the 5' end of SEQ ID NO:1 and said R3 locus consists of GT dinucleotide repeats from nucleotide position 87 from the 5' end of SEQ ID NO:2 of Signal Transducer and Activator of Transcription-6 (STAT-6) gene for use in predicting susceptibility of a human subject to atopic asthma,
   wherein the isolated variants have haplotype 17_14, where the haplotype has 17 repeats on the R1 locus and 14 repeats on R3 locus, and
   wherein the isolated variants have haplotype 23_16, where the haplotype has 16 repeats on the R1 locus and 23 repeats on the R3 locus, and
   wherein the isolated variants have haplotype 24_16, where the haplotype has 24 repeats on the R1 locus and 16 repeats on the R3 locus, and
   wherein these haplotypes are associated with protection from asthma.

* * * * *

UNITED STATES PATENT AND TRADEMARK OFFICE
CERTIFICATE OF CORRECTION

PATENT NO. : 7,671,182 B2 Page 1 of 1
APPLICATION NO. : 10/814002
DATED : March 2, 2010
INVENTOR(S) : Ghosh et al.

It is certified that error appears in the above-identified patent and that said Letters Patent is hereby corrected as shown below:

Title Page, Item (60) should be inserted to read

--Related U.S. Application Data

(60)  Provisional Application Number 60/459,038 filed on March 31, 2003.--

Signed and Sealed this

Twenty-fifth Day of May, 2010

David J. Kappos
*Director of the United States Patent and Trademark Office*